United States Patent [19]

Jacobs

[11] Patent Number: 4,615,360
[45] Date of Patent: Oct. 7, 1986

[54] MEANS PROVIDING SEPARATION OF EXTERIOR SHEATH OF LIQUID ON DISPENSING TIP

[75] Inventor: Merrit N. Jacobs, Fairport, N.Y.

[73] Assignee: Eastman Kodak Company, Rochester, N.Y.

[21] Appl. No.: 772,783

[22] Filed: Sep. 5, 1985

[51] Int. Cl.⁴ .......................... B67C 1/06; B65B 3/04
[52] U.S. Cl. ........................................ 141/18; 141/91; 73/863.24; 222/148; 239/105; 422/64
[58] Field of Search ...................... 141/85–93, 141/1–12, 115–127, 392, 70, 311 A, 18–27, 37–66, 67; 422/64, 100, 104, 63; 73/863.24, 863.41, 864.11; 222/148, 149, 150, 151; 239/104, 105

[56] References Cited

U.S. PATENT DOCUMENTS

| | | | |
|---|---|---|---|
| 3,552,212 | 1/1971 | Ohlin | 73/423 |
| 4,287,155 | 9/1981 | Tersteeg et al. | 422/64 |
| 4,340,390 | 7/1982 | Collins et al. | 422/64 |
| 4,347,875 | 9/1982 | Columbus | 141/392 |

*Primary Examiner*—Houston S. Bell, Jr.
*Attorney, Agent, or Firm*—Dana M. Schmidt

[57] ABSTRACT

There is disclosed apparatus in which an aspirating and dispensing tip is provided with liquid wherein residual liquid is left as a sheath on the exterior of the tip after aspiration. The apparatus is improved to include means exterior of the dispensing tip for separating the sheath into at least two parts without detaching residual liquid physically from the exterior surface, the two parts being separated along the axis of the tip by a dry annular portion of the exterior surface having a suitable width. Such separating means is spaced away from the tip a distance effective to prevent contact of the separating means with either the tip or the liquid of the sheath.

5 Claims, 6 Drawing Figures

U.S. Patent  Oct. 7, 1986  Sheet 1 of 2  4,615,360

MEANS PROVIDING SEPARATION OF EXTERIOR SHEATH OF LIQUID ON DISPENSING TIP

FIELD OF THE INVENTION

This invention relates to apparatus for aspirating liquid into and dispensing aspirated liquid from a dispensing tip. More specifically, it relates to apparatus which provides more uniform volumes during dispensing.

BACKGROUND OF THE INVENTION

In biological fluid analyzers of the type described in U.S. Pat. Nos. 4,287,155, issued Sept. 1, 1981, and 4,340,390, issued July 20, 1982, perfusion has been an occasional but persistent problem. "Perfusion" refers to the movement of dispensed liquid up the exterior surface of the dispensing container, rather than down onto a test element designed to receive the liquid. Perfusion is a problem because liquid contacting such exterior surface alters the volume of liquid that is subsequently dispensed. Perfusion often results in no fluid being dispensed to the slide surface. Because of this problem, studies have been made to locate the cause and to provide solutions. Unfortunately, it appears that there may be a number of possible causes, so that a solution to one of the causes is not necessarily effective in preventing perfusion caused by a different cause. For example, one problem involved process steps that caused a scraping of the exterior surface of the dispensing tip that tended to encourage perfusion. This was a problem even when using tips as described in U.S. Pat. No. 4,347,875, issued on Sept. 7, 1982, that were designed to reduce perfusion by pulling the exterior sheath of liquid away from the tip. Alteration of the analyzer to prevent such scraping prevented perfusion arising from this particular cause, but not necessarily from other causes. It is speculated, however, that all of the causes of perfusion relate to maintaining a continuous film of liquid over a large portion of said exterior surface adjacent the tip aperture.

Thus, prior to this invention there has been a need for a solution that would have more widespread application to the problem of perfusion, whatever its cause.

SUMMARY OF THE INVENTION

I have discovered that perfusion is a problem to the extent that surface liquid, that is, liquid left as a sheath on the surface of the disposable tip after aspirating, is allowed to provide a path for the liquid to flow up the exterior surface of the tip when the liquid is dispensed. To the extent this forms a large wetted surface area, it can easily accept the full dispensed volume (10 µl in most cases), in lieu of it being removed onto a test element. As a result, only some or none of the dispensed volume transfers to the test element. I have further discovered that the problem is solved if the surface liquid is separated into two sheath portions, one comprising a small amount left adjacent the tip orifice, and the other comprising a larger amount spaced from the smaller amount, regardless whether or how a continuous film occurs or is maintained on the tip during aspiration. The small wetted surface area left adjacent to the tip orifice is insufficient to lift away the quantity of liquid that is to be dispensed. Thus, the liquid is transferred to the test element and perfusion is prevented.

More specifically, there is provided apparatus for aspirating liquid into a dispensing container having a dispensing tip and aperture, and means for moving the dispensing tip first into the liquid to permit aspiration, and then away from the liquid to permit dispensing of a prescribed volume, the dispensing tip comprising an end surface through which the dispensing aperture extends, the end surface terminating at an edge. The dispensing tip further includes an exterior surface extending from the end surface edge, the exterior surface being subjected to residual liquid which can form a sheath on the exterior surface when the tip is immersed in the liquid during aspiration and then removed from the liquid. Such apparatus is improved in that it further includes means separate from the tip for separating said sheath into at least two parts, without detaching residual liquid physically from the exterior surface, the two parts being separated along the axis of the tip by a dry annular portion of the exterior surface having a width effective to keep dispensed liquid from joining both parts, the separating means being disposed so that the separated liquid part closest to the platform edge contacts a surface area that can hold only a volume that is negligible compared to the prescribed volume, the separating means being spaced from the tip a distance effective to prevent contact with either the dispensing tip or the sheath of liquid.

Thus, it is an advantageous effect of the invention that the ability of the lower liquid part to attract the dispensed volume is insignificant. Therefore, perfusion is prevented from occurring during dispensing, for whatever reason.

It is a related advantageous effect of the invention that such dispensed volume is maintained constant without the necessity of treating or preventing perfusion as it might be caused by a variety of factors.

Other advantageous effects will be readily apparent from the following Description of the Preferred Embodiments, when read in light of the attached drawings.

DESCRIPTION OF THE PREFERRED EMBODIMENTS

This invention is described particularly in connection with the dispensing of liquid such as serum onto test elements that permit the quantitative analysis of analytes in the liquid. In addition, the invention is useful in any dispensing apparatus or method which aspirates liquid into a dispensing tip and thereafter dispenses some of the liquid, regardless of the nature of the material on which the liquid is dispensed, or the nature of the liquid.

Terms such as "up", "down", "lower", "vertical", "horizontal", and "bottom", as used herein refer to the orientation of parts when the apparatus is positioned in its customary position of use.

Figure 1:
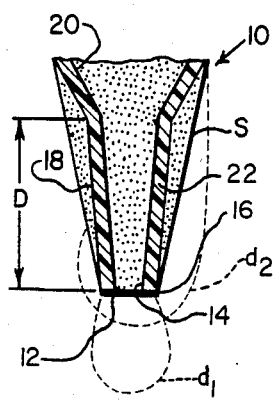
FIG. 1 is a fragmentary sectional view of a dispensing tip and the dispensing problems that occur in the prior art.

Conventionally, a disposable tip, e.g., tip 10 of FIG. 1, is used to aspirate liquid into the tip and then to dispense some of the aspirated liquid, for example, in 10 $\mu$l amounts. The tip is usually a disposable part, to prevent contamination from occurring from one liquid sample to the next. It also features an end surface 12 having an aspirating and dispensing aperture 14, and a sharp edge 16 where surface 12 intersects with exterior surface 18 of the tip angled to surface 12. It is on this latter surface 18 that the sheath S of liquid forms after aspiration while the tip is being withdrawn from the source of liquid. Preferably, the sharpness of edge 16 is controlled as described in the aforesaid U.S. Pat. No. 4,347,875.

One approach to this problem has been to shape tip 10 so that the cone angle of portion 20, spaced from surface 12, is larger than the cone angle for portion 22 adjacent to surface 12. As described in the aforesaid U.S. Pat. No. 4,347,875, this shape encourages sheath S to pull up towards portion 20, away from surface 12, at least if dimension D is properly selected. Although this is effective in many cases to keep the meniscus $d_1$ from perfusing (to the condition shown as $d_2$), it does not always do so. For example, damage to portion 22 can still encourage perfusion to occur, particularly if edge 16 is damaged also. Thus, and particularly if the teachings of the '875 patent are not followed, the dispensing tip 10 sometimes produces a sheath S of liquid. In such a case, when the next quantity of liquid is dispensed, instead of the shape $d_1$ noted by the dotted lines, the quantity tends to perfuse up surface 18 and join with sheath S to produce the shape shown as dotted line $d_2$. Even if quantity $d_2$ touches the test element onto which it is to be transferred, there is enough area to surface 18 that most of $d_2$ is left behind, rather than transferred. In the worst cases, $d_2$ does not even touch the test element.

Figure 2:
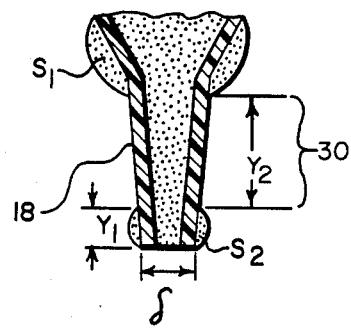
FIG. 2 is a fragmentary sectional view of a dispensing tip similar to that of FIG. 1, but illustrating the present invention.

In accordance with the invention, these drawbacks are prevented by using means separate from the tip 10 to separate the sheath into at least two parts, an upper part $S_1$ and a lower part $S_2$, FIG. 2. The lower part contacts a portion of surface 18 that has a negligible surface area, compared to that required to support the volume of $d_1$. Furthermore, if $S_2$ joins $d_2$ to be dispensed, the volume of $S_2$ adds substantially little to the desired volume. For such volume of 10 $\mu$l, dimension $Y_1$ is preferably no greater than about 900 $\mu$m, for a diameter "delta" that is no greater than about 1020 $\mu$m. The two parts are separated by a dry annular portion 30 of surface 18, such portion having a width $Y_2$ that extends a distance sufficient to keep quantity $d_1$ or $d_2$ from contacting sheath $S_1$. (Upper part $S_1$ can, of course, comprise several individual parts, provided dimension $Y_2$ is maintained.) In a preferred form of the invention, the apparatus used with the invention permits considerable jiggling of the tip between aspiration and dispensing. In such a construction, $Y_2$ preferably extends from about 0.1 cm to about 0.4 cm. This figure will vary as the surface tension of the dispensed liquid varies, and can be decreased even below 0.1 if jiggling is decreased. It is this dry annular portion that ensures that perfusion will not occur because $d_1$ cannot contact $S_2$.

Any means separate from tip 10 can be used to achieve this separation, so long as such means does not contact either tip 10 or sheath S (to prevent contamination). Most preferred is the use of at least one air jet 40, FIG. 3, delivering air at a flow rate sufficient to separate sheath S into the two parts $S_1$ and $S_2$, but without being so strong as to actually physically detach liquid from the tip. (Detachment of liquid could result in liquid falling onto parts of the analyzer, creating contamination when those parts handle a different test element for a different patient's serum.) The interior of the air passage 42 of the jet is designed with a height h and a width 1, FIG. 4, to provide such a flow rate. It is disposed a distance $Y'_1$, FIG. 3, above the plane of surface 12 of the tip, to ensure that the blowing air does not cause withdrawal of liquid from tip 10 by a venturi effect. To this end, $Y'_1$ is preferably at least as much as 1270 $\mu$m, to produce a $Y_1$ value, FIG. 2, of about 380 $\mu$m, but can be as large as 1780 $\mu$m, to produce a $y_1$ value of as much as 900 $\mu$m.

Figure 3:
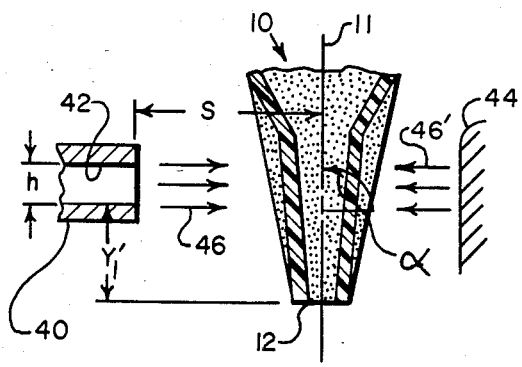
FIG. 3 is a schematic sectional view similar to that of FIG. 2, to which has been added some of the apparatus that provides the result of FIG. 2.
Figure 4:
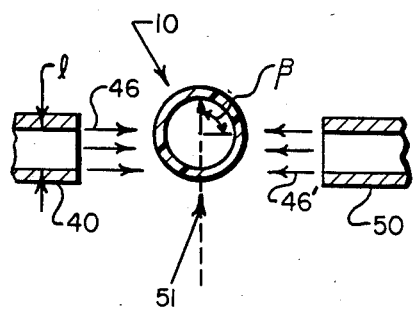
FIG. 4 is a schematic sectional view taken generally orthogonal to the axis of the tip shown in FIG. 3, illustrating a more preferred apparatus of the invention.

A single jet 40 can be used to create air flow 46, FIG. 3, with a deflecting surface 44 causing some back flow, arrows 46', or two such jets 40 and 50 can be used, FIG. 4. In either case, preferably tip 10 moves through the air flow with its axis 11, FIG. 3, generally perpendicular to the flow arrows 46, that is, with angle alpha being $\pm 10°$ from 90°. In addition, most preferably the direction of movement of tip 10, arrow 51 of FIG. 4, is also generally perpendicular to flow arrows 46, that is, so that angle beta is $90° \pm 10°$.

Figure 5:
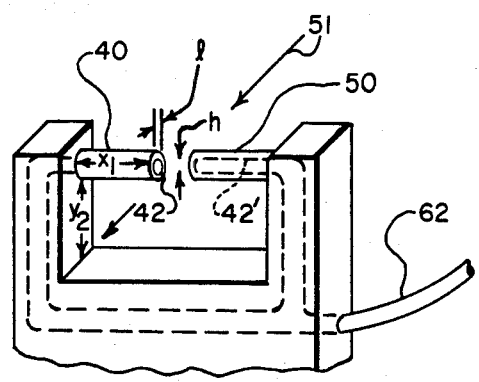
FIG. 5 is a fragmentary perspective view illustrating one embodiment of air jets useful in this invention.

FIG. 5 further illustrates a useful embodiment for a two-jet arrangement, in which air pump 60 provides air to the jets as directed by conventional controls, not shown, and air hose 62. The dimensions 1 and h of passages 42 and 42' most preferably are about 0.4 cm and 0.03 cm, respectively, and $x_1$ and $Y_2$ in such a design are 1.4 cm and 0.7 cm, respectively. The spacing distance Z, FIG. 3, as a tip moves through the air flow via the direction of arrow 51, is preferably about 0.17 cm. The amount of dwell time of a tip 10, FIG. 4, within air flow 46 and 46' is most preferably at least 0.2 sec.

The amount of air flow necessary to achieve the above results will of course vary, depending on a number of conditions readily apparent to one skilled in the art. One of these is the actual design of the air jets. That is, to the extent the design confines the air exiting from the air jet to stay within the vicinity of the tip, less air flow is necessary than a design that allows the air flow to quickly dissipate.

To the extent spacing distance Z, FIG. 3, is decreased, less flow rate is required. For the preferred spacing distance Z that varies from 500 $\mu$m to about 0.4 cm, and for the particular design shown wherein $Y_1$ is between about 380 and about 900 $\mu$m, it is estimated that the separation of the sheath into the two parts spaced as described above, occurs most readily if the air flow from the two jets is from about 14 L/min to about 55 L/min. This range of flow rates was determined by establishing that the air pressure needed to achieve such results, was between about 4 cm of $H_2O$ and about 13 cm of $H_2O$ above atmosphere. Since the same air pressure gauge produced 5 cm of $H_2O$ at a flow of 0.68 ft$^3$/min and 2.54 cm of $H_2O$ at a flow of 0.3 ft$^3$/min, such pressures of 4 and 13 cm correspond to a flow rate of about 14 to about 55 L/min.

Figure 6:
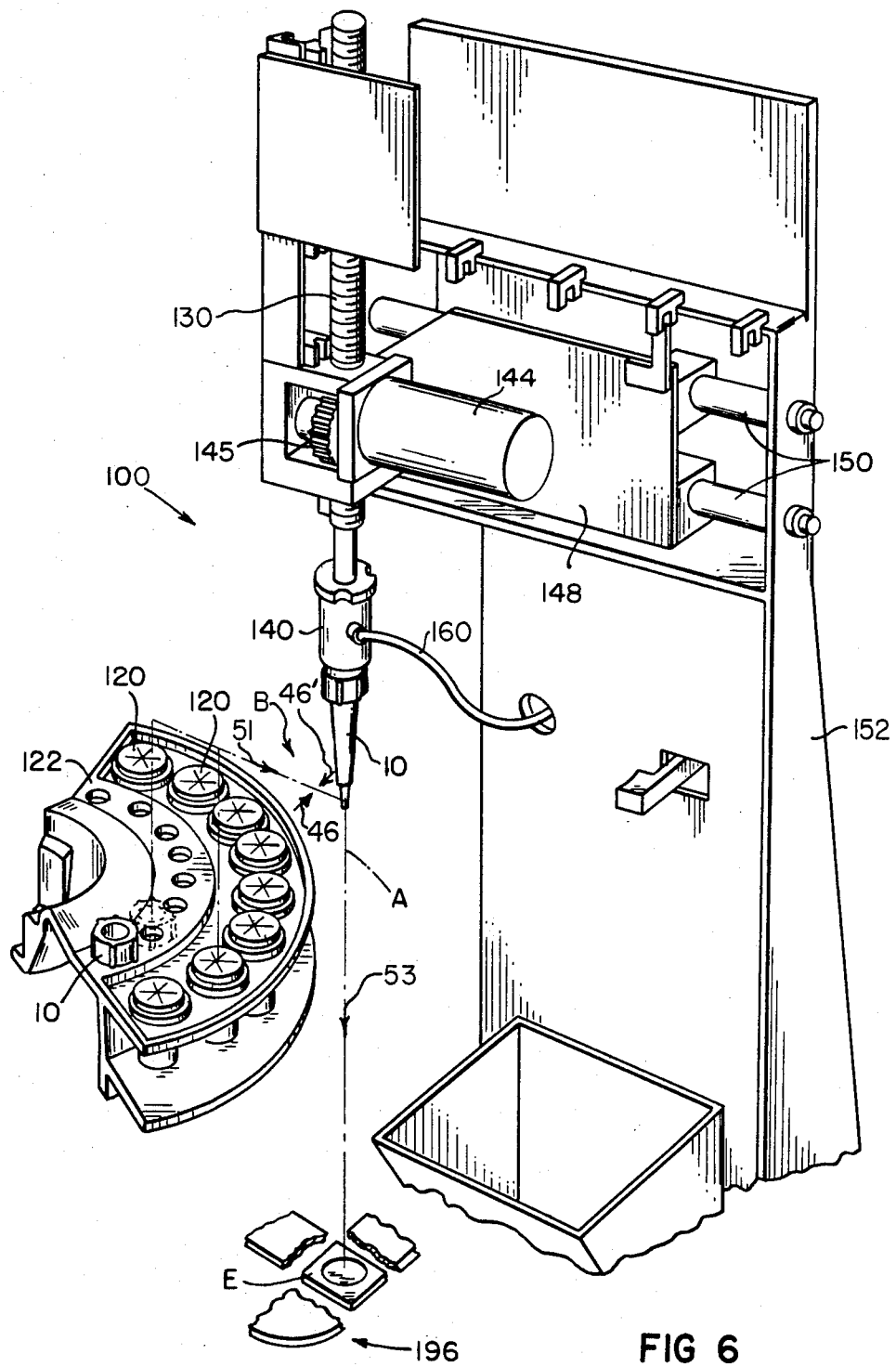
FIG. 6 is a fragmentary perspective view of an analyzer adapted to include this invention.

The manner in which the preceding apparatus can fit in with the rest of a conventional analyzer 100 is shown in FIG. 6. Such analyzer supplies a source of serum in the form of capped cups 120 mounted in a tray 122 that also supplies tips 10. A probe 140 is mounted on a screw 130 that is raised and lowered by a gear 145 actuated by motor 144. The motor and gear are carried by a car 148 on pairs of rails 150 on a frame 152. A hose 160 supplies a partial vacuum or a partial pressure to probe 140 and tips 10 mounted thereon.

Probe 140 is thus caused to trace paths that lie in plane A. Specifically, tip 10 is picked up by the probe, immersed into cups 120 and then moved sideways, arrow 51, until the probe is ready to descend, as per arrow 53, to the test element E held by a member 196 below. It is along path 51 and specifically at position B that the jets 40 and 50 (not shown) are preferably located to direct air flow 46 and 46′ as shown. Most preferably, the jets are not located along arrow 53, as such would be apt to cause venturi displacement of liquid out of the tip 10.

Such an analyzer using the air jets as described has been found to provide a distinct improvement in uniformity of dispensed volumes. This was noted by repeating tests either with the air pump on or off, using tips prepared as described in the aforesaid '875 patent. With the air pump on, the % of occasions when dispensed volume was found to vary significantly dropped to 0.17%, compared to 2.9% when the air pump was off. The specific figures were, for 600 tests with air on, the number of significant deviations was 1. For 588 tests with air off, the number of significant deviations was 17. (The spacing distance Z, FIG. 3, was 0.33 cm and the air flow rate was about 2.8 standard cubic meters/hour.)

The invention has been described in detail with particular reference to preferred embodiments thereof, but it will be understood that variations and modifications can be effected within the spirit and scope of the invention.

What is claimed is:

1. In apparatus for aspirating liquid into a dispensing container having a dispensing tip and aperture, and means for moving said container and dispensing tip first into the liquid to permit aspiration, and then away from the liquid to permit dispensing of a prescribed volume, said dispensing tip comprising an end surface through which said dispensing aperture extends, said end surface terminating at an edge, said extending tip further including an exterior surface extending from said end surface edge, said exterior surface being subjected to residual liquid which can form a sheath thereon when said tip is immersed in the liquid during aspiration and then removed from the liquid;

the improvement wherein said apparatus further includes means separate from said tip for separating said sheath into at least two parts, without detaching residual liquid physically from said exterior surface, said two parts being separated along the axis of said tip by a dry annular portion of said exterior surface having a width effective to keep dispensed liquid from joining both parts, said separating means being disposed so that the separated liquid part closest to said platform edge contacts a surface area on said tip that holds only a volume that is negligible compared to said prescribed volume, said separating means being spaced from said tip a distance effective to prevent contact with either said dispensing tip or said sheath of liquid.

2. Apparatus as defined in claim 1, wherein said separating means includes an air jet delivering air at a flow rate sufficient to separate said sheath into two parts without physically detaching said liquid.

3. In apparatus for aspirating liquid into a dispensing container having a dispensing tip and aperture, and means for moving said container and dispensing tip first into the liquid to permit aspiration, and then away from the liquid to permit dispensing, said dispensing tip comprising an end surface through which said dispensing aperture extends, said end surface terminating at an edge, said dispensing tip further including an exterior surface extending from said end surface edge, said exterior surface being subjected to residual liquid left as a sheath thereon when said tip is immersed in the liquid during aspiration and then removed from the liquid;

the improvement wherein said apparatus further includes at least one air jet spaced from and aimed at said tip, and means for delivering air to said jet at a flow rate sufficient to divide said sheath into two parts separated along the axis of said tip a distance of at least 0.1 cm, without physically detaching said liquid, the part of the liquid which is located adjacent said aperture extending away from said aperture a distance no greater than 900 μm.

4. Apparatus as defined in claim 2 or 3, and further including means for holding said tip within said air flow for at least 0.2 seconds.

5. Apparatus as defined in claim 2 or 3, wherein said distance of said jet from tip is from about 0.05 cm to about 0.4 cm.

* * * * *